US006746414B1

(12) United States Patent
Devreese

(10) Patent No.: US 6,746,414 B1
(45) Date of Patent: Jun. 8, 2004

(54) JOINT FOR A KNEE BRACE INCORPORATING A LOCKING MECHANISM

(75) Inventor: Serge Lucien Pierre Michel Devreese, Theux (BE)

(73) Assignee: Generation II Orthotics, Inc., Richmond (CA)

( * ) Notice: Subject to any disclaimer, the term of this patent is extended or adjusted under 35 U.S.C. 154(b) by 0 days.

(21) Appl. No.: 09/519,306

(22) Filed: Mar. 6, 2000

(51) Int. Cl.$^7$ .................................................. A61F 5/00
(52) U.S. Cl. ............................................ 602/26; 602/5
(58) Field of Search ............................... 602/5, 16, 23, 602/26, 27; 128/846, 882

(56) References Cited

U.S. PATENT DOCUMENTS

| 3,902,482 | A |   | 9/1975  | Taylor |         |
|-----------|---|---|---------|--------|---------|
| 4,915,098 | A | * | 4/1990  | Young  | 602/16  |
| 5,267,950 | A | * | 12/1993 | Weddendorf | 602/26 |
| 5,277,698 | A |   | 1/1994  | Taylor |         |
| 5,302,169 | A |   | 4/1994  | Taylor |         |
| 5,312,411 | A |   | 5/1994  | Steele et al. | |
| 5,356,370 | A |   | 10/1994 | Fleming |        |
| 5,358,469 | A | * | 10/1994 | Patchel | 602/23 |
| 5,400,806 | A |   | 3/1995  | Taylor |         |
| 5,425,700 | A | * | 6/1995  | Aaserude | 602/26 |
| 5,562,605 | A |   | 10/1996 | Taylor |         |

* cited by examiner

Primary Examiner—Michael A. Brown
(74) Attorney, Agent, or Firm—William Michael Hynes; Townsend and Townsend and Crew LLP

(57) ABSTRACT

An orthopaedic knee brace comprising an upper arm and a lower arm securable to a wearer's leg above and below the knee joint. There is a pivotable joint at the ends of the arms to allow flexing of the knee by pivoting movement of the arms. A locking mechanism is provided to control pivoting of the joint to lock one of the upper or lower arms relative to the joint while automatically unlocking the other arm to permit pivoting movement of the other arm about the joint. The joint and locking mechanism co-operate to form a light weight structure that operates smoothly to imitate the complex bending motion of the knee while supporting the knee.

11 Claims, 4 Drawing Sheets

JOINT FOR A KNEE BRACE INCORPORATING A LOCKING MECHANISM

FIELD OF THE INVENTION

This invention relates generally to joints for orthopaedic braces and more particularly to a mechanical joint for a knee brace incorporating a locking mechanism to control and co-ordinate movement of the joint.

BACKGROUND OF THE INVENTION

The human knee is not a simple hinge joint. The knee is capable of gliding, rocking and rotational movement that make it difficult to imitate in a simple mechanical joint. When the knee bends and straightens during walking or running, the femur and tibia interact in sliding, gliding and rotational movement relative to one another. It is only when the leg is straightened and supporting the weight of the body that the knee joint is locked. Thus, the natural knee joint has a point of pivot that moves about as the leg is bent and straightened with the knee providing a restricted universal action unless firmly locked as described.

When bracing the knee, it is generally desirable that the supported knee be allowed to operate in as natural a manner as possible so as not to impart abnormal forces across the joint during activity and to allow the wearer to bend and straighten the leg in a normal manner.

A leg brace requires a mechanical joint that will support the knee and reproduce as closely as possible the complex pivoting motion of the knee. At the same time, the mechanical joint must not be so heavy, bulky or complex that the normal movement of the knee is impeded. Various mechanical joints have been developed to satisfy the above requirements.

U.S. Pat. No. 3,902,482 issued Sep. 2, 1975 teaches an orthopaedic brace having a mechanical joint interconnecting brace arms that attach to the legs of the wearer above and below the knee. The joint is lightweight, relatively simple in construction and does a good job of imitating the motion of the knee. This same joint has been used in other patented braces or bracing methods such as U.S. Pat. No. 5,277,698 issued Aug. 18, 1993, U.S. Pat. No. 5,302,169 issued Apr. 12, 1994 and U.S. Pat. No. 5,562,605 issued Oct. 8, 1996. All these patents and the present invention are commonly owned.

While the mechanical joint disclosed in the above references does a good job of reproducing the natural motion of the human knee joint, the joint suffers from the drawback that it permits knee joint movement that is not natural at certain positions of the mechanical joint. For example, when the knee is straightened and locked, the lower leg should not be able to pivot. In flexion, the two halves of the joint tend to loosen relative to each other in the anterior/posterior plane which is clearly undesirable for a knee brace intended to support and guide the knee. To address this problem, the knee brace hinge was modified to include an elastic link extending between the lower arm and the joint that tends to resist movement of the lower arm when the knee is locked. This is an imperfect solution as resistance to movement of the lower arm is also present when movement of the lower arm is desired.

SUMMARY OF THE INVENTION

Accordingly, there is a need for a knee brace and mechanical joint that accurately mimics the complex movement of the human knee joint and at the same time does a complete job of bracing and supporting the knee over the full range of motion of the knee. In some positions, this involves locking one or the other of the brace arms from movement depending on the extent of flexing of the knee.

The present invention provides an orthopaedic knee brace that incorporates a locking mechanism that automatically locks one of the brace arms while unlocking the other arm to more accurately imitate the motion of the human knee and offer better bracing and support for the knee.

Therefore, the present invention provides in an orthopaedic knee brace comprising an upper arm and a lower arm securable to a wearer's leg on opposite sides of the knee joint and a pivotable joint at the ends of the arms to allow pivoting of the knee by pivoting movement of the arms, the improvement comprising:

a locking mechanism to control pivoting of the joint to lock one of the upper or lower arms relative to the joint while automatically unlocking the other arm to permit pivoting movement of the other arm about the joint.

The brace of the present invention with its joint and locking mechanism provides a lightweight, reliable structure that is able to smoothly pivot to imitate the complex motion of the knee while fully supporting the knee.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

Figure 1:
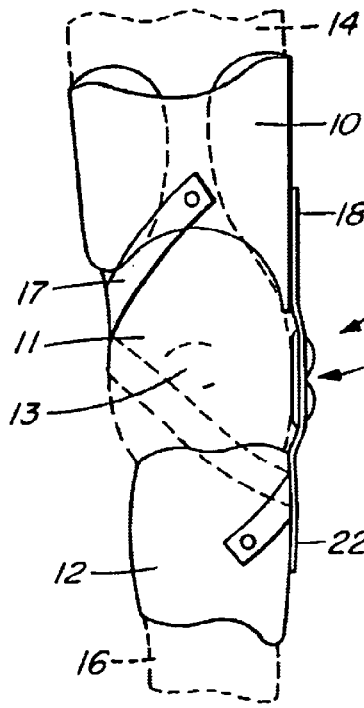
FIG. 1 is a front view showing a preferred embodiment of the brace of the present invention in position on the leg of a wearer.

Referring to FIG. 1, there is shown a brace 2 attached to a leg 11 of a wearer to lend support to the knee 13. The brace is shown having an upper cuff 10 that fits about the thigh 14 of a user and a lower cuff 12 that fits about the upper calf 16. A strap 17 extends between the upper and lower cuffs and wraps about the leg to retain the brace 2 on the leg. This attachment scheme is entirely conventional and other methods of securing the brace 2 to the leg are possible.

Figure 2:
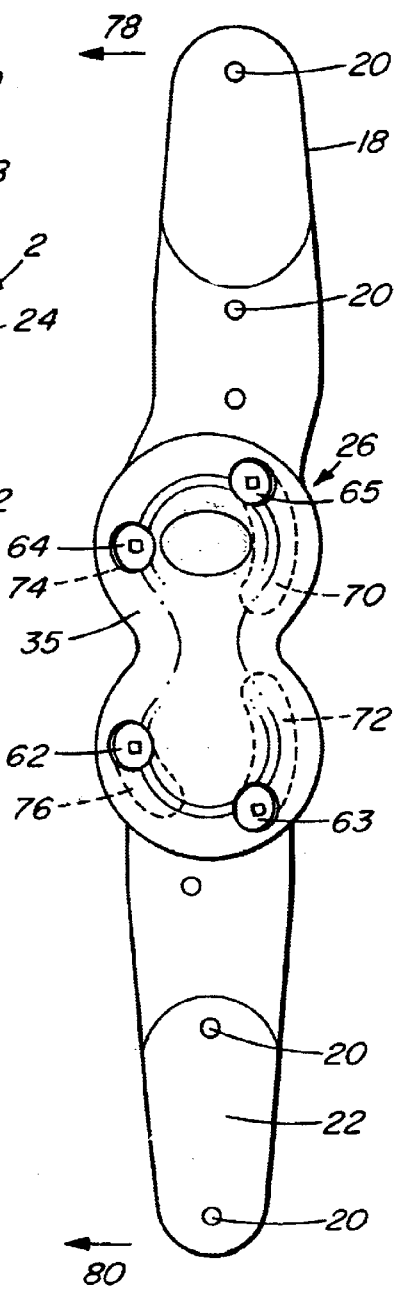
FIG. 2 is a front view of the brace according to the invention.

Upper cuff 10 is mounted to an upper arm 18 comprising essentially a rigid metal strip that is located by screws extending through the upper cuff 10 to engage in threaded openings 20 in arm 18 (FIG. 2). A lower arm 22 is attached to lower cuff 12 in a similar manner.

A pivotable joint 24 is formed at the ends of arms 18 and 22 to allow pivoting of the knee by pivoting movement of the arms. Joint 24 incorporates the novel locking mechanism of the present invention which acts to control pivoting of the joint to lock one of arms 18 or 22 in place relative to the joint while automatically unlocking the other arm to permit free pivoting movement as will be explained in more detail below.

Figure 3:
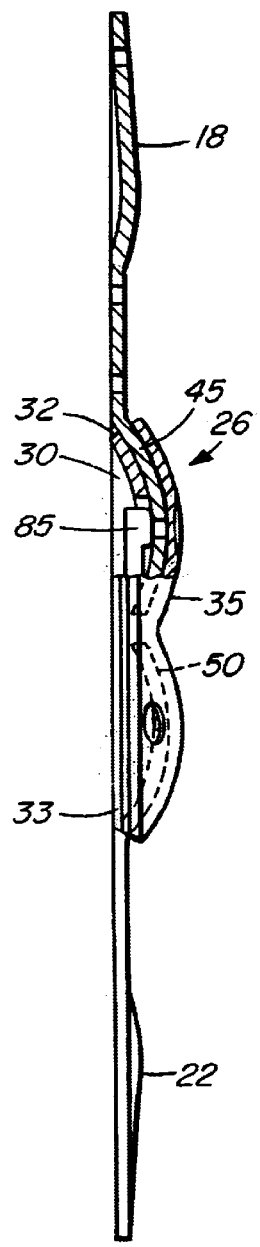
FIG. 3 is a side elevation view through the brace with some portions in cross-section.

As shown most clearly in FIG. 3, joint 24 is formed from bearings 26 and 28 which pivotally connect arms 18 and 22 to a link 30 which extend across the knee joint. Link 30 is formed from substantially circular bearing plates 32 and 33 that are joined together. The lower end of upper arm 18 is formed with a bearing plate 45 and the upper end of lower arm 22 is formed with a bearing plate 50.

Figure 4:
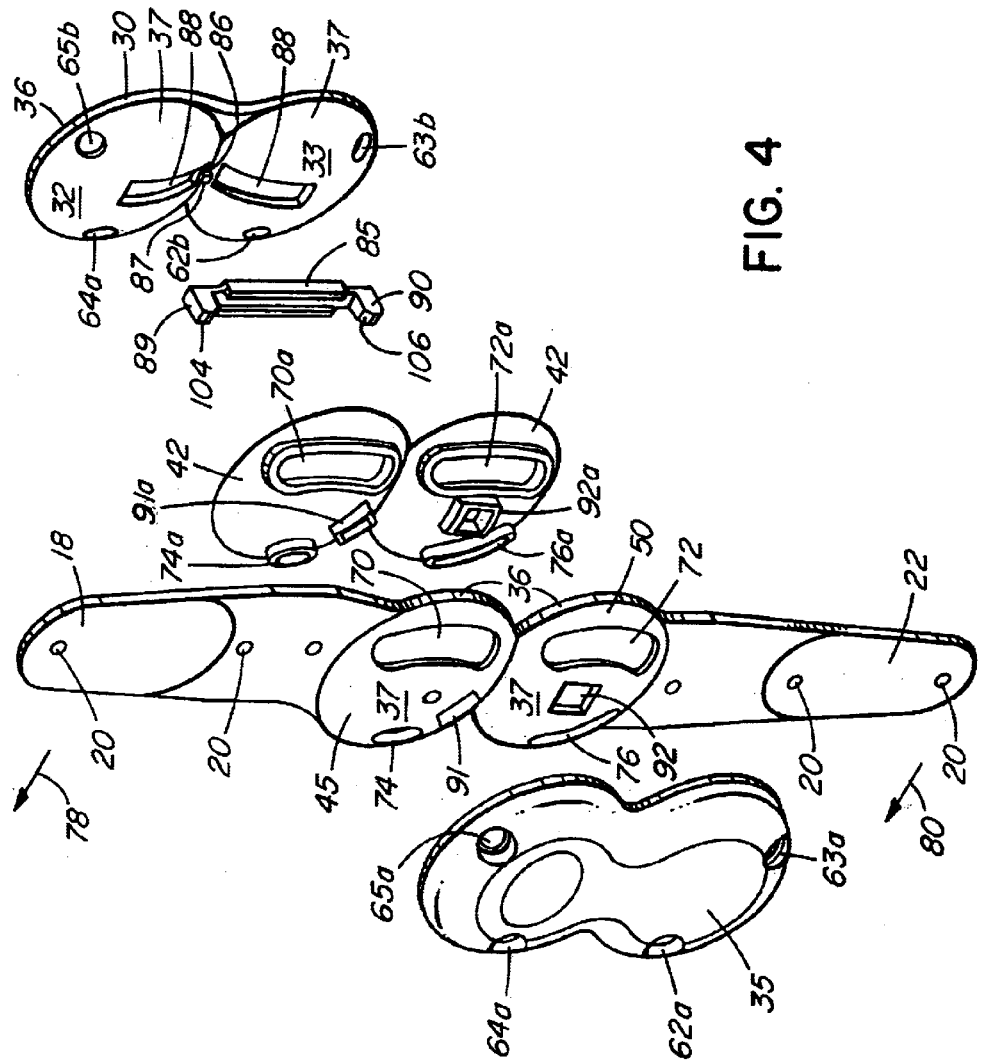
FIG. 4 is an exploded view showing the component parts of a preferred embodiment of the present invention.

The various bearing plates 32, 33 of link 30 and the bearing plates 45 and 50 of the arms are all generally circular and have inner concave faces 36 and outer convex faces 37. The bearing plates 45 and 50 of the arms are adapted to overlap and closely fit the bearing plates 32 and 33, respectively, of link 30 to define dual bearings 26 and 28. The inner concave surfaces 36 of plates 45 and 50 are readily slidable over the outer convex surfaces 37 of plates 32 and 33 to provide a smooth pivoting action. Preferably, as best shown in FIG. 4, inserts 42 made from a suitable low friction material such as plastic or the like and shaped appropriately are inserted between arm bearing plates 45, 50 and link bearing plates 32 and 33 to promote smooth pivoting movement of the joint. The inserts are preferably formed to be press fitted into place on the inner concave faces 36 of bearing plates 45 and 50.

A cover 35 is also preferably provided to cover the arm bearing plates 45 and 50 as best shown in FIGS. 3 and 4. Cover 35 and link 30 act to sandwich plates 45 and 50 therebetween for pivotal movement. Cover 35 is not required but the cover does serve to protect and hide the movable bearing plates 45 and 50 of joint 24.

Plates 32 and 45 of bearing 26 and plates 33 and 50 of bearing 28 are maintained in face-to-face sliding contact by means of pivot pins. As best shown in FIG. 2 and 4, the pivot pins preferably comprise bolts 62 and 63 that extend through clear holes 62a and 63a, respectively, in cover 35 to engage threaded holes 62b and 63b in link 30. In a similar manner, bolts 64 and 65 extend through clear holes 64a and 65a in cover 35 to engage threaded holes 64b and 65b in link 30.

Arm bearing plates 45 and 50 are formed with arcuate slots 70,72,74 and 76 to permit passage of the bolts through the plates. The bolts and slots co-operate to define a plurality of pivoting axes for arms 18 and 22, as indicated by arrows 78 and 80, which are shiftable to accommodate the natural pivotal movement of the knee.

In the event that cover 35 is not present, the pivot pins can be posts that extend outwardly from the convex faces 37 of link 30 with enlarged heads that slidably engage the outer or convex faces 37 of bearing plates 45 and 50 to hold the bearing plates against separation from link 30.

If low friction inserts 42 are present, they are also formed with appropriate slots 70a,72a,74a and 76a to accommodate the pivot pins.

The foregoing description of the brace structure is conventional and is generally disclosed in commonly owned patents such as U.S. Pat. No. 3,902,482 issued Sep. 2, 1975, U.S. Pat. No. 5,302,169 issued Apr. 12, 1994 and U.S. Pat. No. 5,400,806 issued Mar. 28, 1995.

According to the invention, joint 24 of brace 2 includes a locking mechanism to control the pivoting of the joint to lock one of the upper or lower arms 18, 22 relative to the joint while automatically unlocking the other arm to permit pivoting movement of the other arm about the joint. The locking mechanism acts to lock lower arm 22 in a default position relative to joint 24 until upper arm 18 is pivoted to a pre-determined position relative to the joint at which point the locking mechanism automatically locks upper arm 18 relative to the joint while lower arm 22 is unlocked to pivot. Lower arm 22 is free to pivot until the lower arm is pivoted back to its default position whereupon upper arm 18 is automatically unlocked and lower arm 22 is locked.

Figure 5:
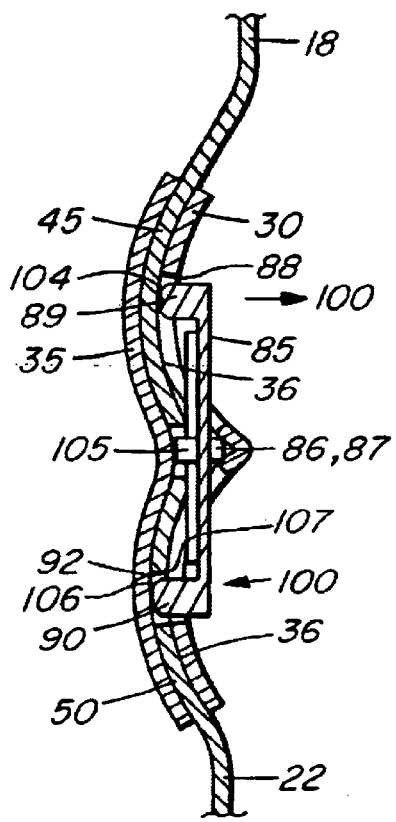
FIG. 5 is a detail section view through the brace joint that shows the position of the rocker arm of the locking mechanism to lock the lower arm and permit free pivoting of the upper arm.
Figure 5A:
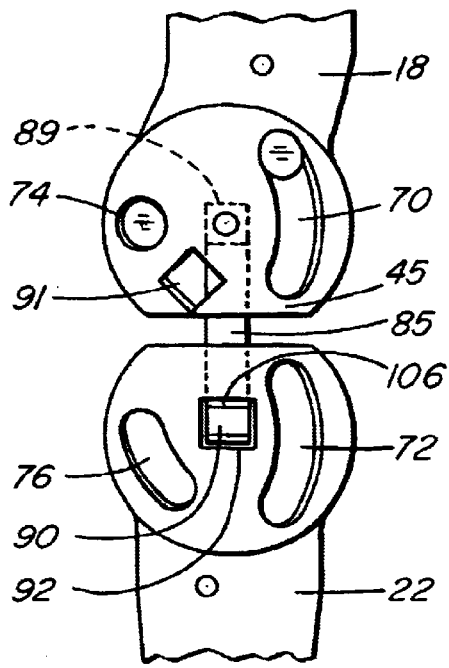
FIG. 5a is a front schematic view of the brace corresponding to the position shown in FIG. 5.

The default locked position of the lower arm 22 is illustrated in FIGS. 5 and 5a. When the knee is straightened, the leg is essentially straight and the lower arm 22 is aligned with the lower leg in an essentially vertical position.

Figure 6:
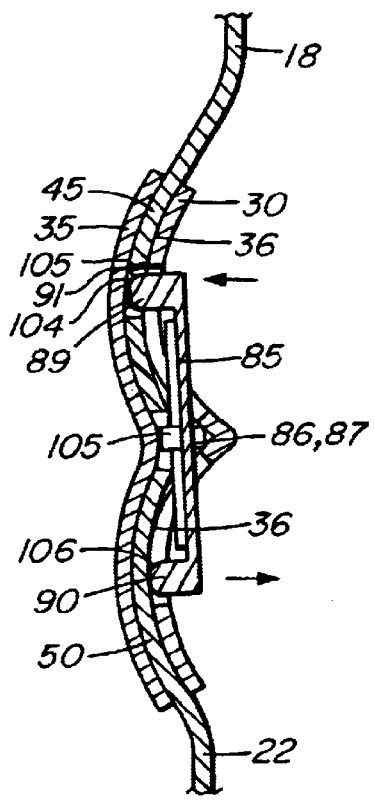
FIG. 6 is a detail section view through the brace joint that shows the position of the rocker arm of the locking mechanism to lock the upper arm and permit free pivoting of the lower arm.
Figure 6A:
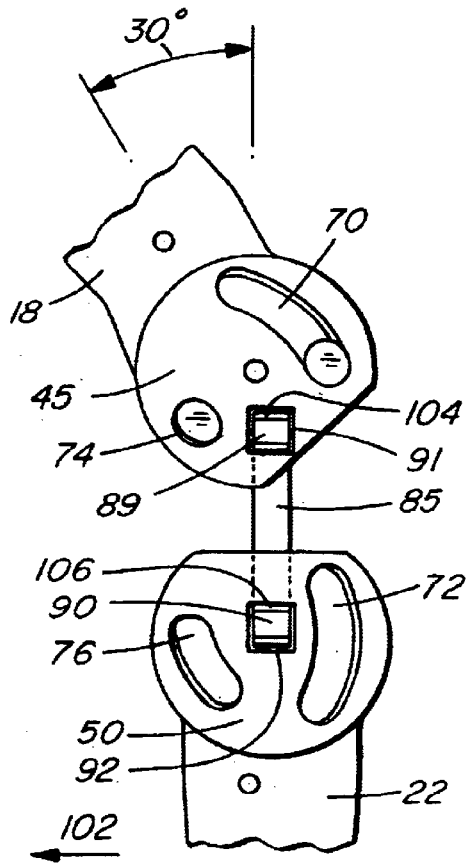
FIG. 6a is a front schematic view of the brace corresponding to the position shown in FIG. 6.

The pre-determined position of upper arm 18 that unlocks lower arm 22 occurs when the knee is flexed such that the upper arm is at an angle of approximately 40 degrees to the still essentially vertical lower arm as best shown in FIG. 6a.

Automatic locking and unlocking of the upper and lower arms at the above-described positions allows the knee brace of the present invention to better support and control the movement of the knee so that the brace permits only natural knee movements. By virtue of the automatic locking of the upper and lower arms depending on their pivotal position, the knee brace prevents the arms from being forced past the normal range of knee movements.

As best shown in FIG. 4, in a preferred embodiment, the locking mechanism of the present invention comprises a rocker arm 85 positioned for pivotal movement about a pivot point adjacent the bearing plates 45,50 of the arms 18,22. In the illustrated arrangement, the pivot point 86 for the rocker arm is formed on link 30 and preferably comprises a block of resilient material 87 fastened to link 30 to absorb vibration and noise. Slots 88 are cut through bearing plates 32 and 33 of link 30 to accommodate pivotal movement of rocker arm 85 on pivot point 86 through the generally spherical bearing plates. In addition, as best shown in FIGS. 5 and 6, cover 35 is preferably provided with a similar block of resilient material 105 which extends inwardly to engage rocker arm 85. The rocker arm is thereby sandwiched between resilient blocks 87 and 105 to absorb vibration and noise to facilitate smooth pivoting of the rocker arm.

Rocker arm 85 has upper and lower protrusions 89 and 90, respectively, at opposite ends of arm 85 on opposite sides of pivot point 86. In the illustrated embodiment, protrusions 89 and 90 are shaped and dimensioned to be generally rectangular to be received in generally rectangular cavities formed on the concave inner face 36 of each of the arm bearing plates 45 and 50. In particular, bearing plate 45 is formed with a cavity 91 to receive protrusion 89 and bearing plate 50 is formed with a cavity 92 to receive protrusion 90. As best shown in FIG. 4, if low friction inserts 42 are used, the inserts are also formed with cavities 91a and 92a that are aligned with and fit into the corresponding cavities 91 and 92 formed in the arm bearing plates 45 and 50.

As best shown in FIGS. 5, 5a, 6 and 6a, the concave inner faces 36 of bearing plates 45 and 50 act as cam surfaces that engage protrusions 89 and 90 to bias rocker arm 85 such that one of the protrusions is always inserted into a cavity of one of the bearing plates to lock the arm associated with the bearing plate. For example, FIGS. 5 and 5a are section and front views, respectively, of the joint in a position in which upper arm 18 is free to pivot and lower arm 22 is locked in place in a substantially vertical orientation. Lower arm 22 is locked in position by virtue of lower rectangular protrusion 90 being inserted into rectangular cavity 92 on bearing plate 50. Upper protrusion 89 is free to slide over the concave inner face 36 of bearing plate 45 which permits movement of arm 18. Inner face 36 acts to bias rocker arm 85 in the direction indicated by arrows 100 to ensure that lower protrusion 90 remains in cavity 92 to lock the lower arm.

Cavities 91 and 92 are positioned and oriented on their respective bearing plates to define the locked position of the upper and lower arms. Note particularly in FIGS. 6 and 6a that as upper arm 18 is rotated associated bearing plate 45 rotates such that when arm 18 is rotated to a pre-determined angle of approximately 40 degrees to vertical, cavity 91 is aligned with and adjacent upper protrusion 89 of rocker arm 85. At this position, either of arms 18 or 22 is free to pivot. Whichever arm moves will result in the protrusion adjacent the bearing plate for that arm moving out of the bearing plate cavity to engage the inner concave surface 36 of the bearing plate causing rocker arm 85 to pivot and the opposite protrusion to be inserted into the other cavity to lock the other arm. For example, if lower arm 22 is rotated in the direction indicated by arrow 102, protrusion 90 will move out of cavity 92 to slide freely on inner concave face 36 of bearing plate 50. At the same time, protrusion 90 moving on face 36 will cause rocker arm 85 to pivot about point 86 so that protrusion 89 will be inserted into cavity 91 to lock bearing plate 45 and upper arm 90 in the position indicated in FIG. 6a.

To assist in the smooth movement of the rocker arm protrusions out of the cavities, both the protrusions and cavities are preferably formed with sloped surfaces. As best shown in FIGS. 5 and 6, upper protrusion 89 has a rounded contoured upper front edge 104 adapted to slide over a correspondingly contoured lip 105 at an upper edge of cavity 91. In a similar manner, lower protrusion 90 has a rounded upper front edge 106 adapted to slide over rounded lip 107 of cavity 92. Except for these cooperating rounded or sloped surfaces, protrusions 89 and 90 and cavities 91 and 92 have generally vertical sides to ensure that a protrusion is held locked within a cavity until such time as the bearing plates 45 and 50 are properly positioned to align both cavities with both protrusions, and one of the arms 18 or 22 is rotated in a direction that causes the rounded surfaces of a cavity and protrusion to engage and slide over each other.

From the above description, it will be apparent that the action of rocker arm 85 causes automatic locking of one arm against movement with respect to joint 24 while simultaneously unlocking the other arm for free pivoting. In this fashion, the knee brace of the present invention offers improved support for the knee as the locking of the upper and lower arms of the brace is designed to correspond to the normal range of movement of the knee joint so as to prevent abnormal anterior/posterior movement.

Although the present invention has been described in some detail by way of example for purposes of clarity and understanding, it will be apparent that certain changes and modifications may be practised within the scope of the appended claims.

I claim:

1. An orthopedic knee brace comprising:
   an upper arm and a lower arm securable to a wearer's leg above and below the knee joint;
   a pivotal joint at the ends of the arms to allow flexion of the knee by pivoting movement of the arms, the pivotal joint being defined by a bearing plate on an end of an each arm near the knee joint, a link the extending across the joint and having a bearing plate on each opposite end thereof, the bearing plates of the arms overlapping the bearing plates of the link to provide dual bearings, and pivot pins the interconnecting the bearing plates of each of the dual bearings to provide each of the dual bearings with a plurality of transverse axes of pivot which are shiftable to accommodate the natural pivotal movement of the knee;
   a locking mechanism the to the control pivoting of the joint to lock one of the upper or lower arms relative to the joint while automatically unlocking the other arm the to permit pivoting movement of the other arm about the joint, the locking mechanism comprising:
      a rocker arm position for pivotal movement about a pivot point adjacent the bearing plates of the arms, the rocker arm having protrusions on opposite sides of the pivot point;
      a cavity formed in each of the armed bearing plates to receive one of the protrusions; and
      cam surfaces formed on each of the arm the bearing plates to engage the protrusions to bias the rocker arm such that one of the protrusions is inserted into a cavity of one of the bearing plates to the prevent movement of the arm to which said bearing plate is attached, the other protrusion sliding freely on the cam the surface of the other bearing plate to permit pivotal movement of the other arm whereby the cavities are positioned to defining the locked position of the upper and lower arms.

2. In an orthopedic knee brace comprising:
   an upper arm securable to a wearer's leg upward of the knee joint;
   a lower arm securable to a wearer's leg below the knee joint; and,
   a joint overlying the knee between the upper arm and the lower arm,
   the improvement to the joint overlying the knee comprising:
      a joint overlying the knee formed from a link and first and second spaced apart bearings pivotally connecting the upper arm and the lower arm to spaced apart positions on the link, respectively;
   the first bearing connecting the link of the joint and the upper arm;
   the second bearing connecting the link of the joint and the lower arm at a position spaced apart from the first bearing;
   an upper locking mechanism to control pivoting of the first bearing to lock the upper arm relative to the first bearing at a first in default position;
   a lower locking mechanism to control the pivoting of the second bearing to lock the lower arm relative to the second bearing at a second default position; and,
   a locking mechanism for locking the upper locking mechanism and unlocking the lower locking mechanism or unlocking the upper locking mechanism and locking the lower locking mechanism;
   whereby the joint emulates the complex pivotal motion of the knee.

3. The improvement to the orthopedic knee brace of claim 2 further including:
   the unlocking the upper locking mechanism and locking the lower locking mechanism occurs when the knee is straightened.

4. The improvement to the orthopedic knee brace of claim 2 further including:

the locking the upper locking mechanism and unlocking the lower locking mechanism occurs when the knee is flexed such that the upper arm is at an angle of approximately 40 degrees to the lower arm.

5. The improvement to the orthopedic knee brace of claim 2 further wherein the interlocking mechanism comprises:

a rocker arm positioned for pivotal movement relative to the link adjacent the first bearing and the second bearing, the rocker arm having first and second protrusions on opposite sides of the link;

a first cavity formed to the upper arm adjacent the link to receive the first protrusion;

a second cavity formed to the lower arm adjacent the link to receive this second protrusion;

cam surfaces for engagement with the rocker arm protrusions such that when one of the protrusions is inserted into a cavity of one of the arms the other protrusion slides freely on cam surfaces, whereby the cavities are position to define the lock to position of the upper and lower arms.

6. The improvement to the orthopedic knee brace of claim 5 further including:

the rocker arm positioned for pivotal movement pivots on the link.

7. The improvement to the orthopedic knee brace of claim 5 further including:

the protrusions of the rocker arm having sloped surfaces to facilitate movement of the first and second protrusions out of the first and second cavities.

8. The improvement to the orthopedic knee brace of claim 2 further including:

the first and second bearings include opposing concave-convex faces generally defining spherical members.

9. The improvement to the orthopedic knee brace of claim 2 further including:

a cover plate is mounted overlying the joint.

10. The improvement to the orthopedic knee brace of claim 2 further including:

the first and second bearings include low friction surfaces for low friction movement of the respective bearings.

11. The improvement to the orthopedic knee brace of claim 10 further including:

the low friction surfaces include inserts fitted between the first and second bearings.

* * * * *